United States Patent [19]
Yamamura et al.

[11] Patent Number: 5,827,862
[45] Date of Patent: Oct. 27, 1998

[54] AGENT FOR PROPHYLAXIS OR TREATMENT OF CATARACT

[75] Inventors: Yoshitaka Yamamura, Itano-gun; Tatsuya Yamashita, Tokushima; Shigeki Nakamura, Komatsushima; Toshiyuki Onogawa, Naruto; Yoshihisa Yamada, Naruto; Kenji Tsujimae, Tokushima; Hidenorii Ogawa, Itano-gun; Toyoki Mori, Naruto; Michiaki Tominaga, Itano-gun, all of Japan

[73] Assignee: Otsuka Pharmaceutical Company, Limited, Tokyo, Japan

[21] Appl. No.: 507,333

[22] PCT Filed: Feb. 22, 1994

[86] PCT No.: PCT/JP94/00265

§ 371 Date: Aug. 23, 1995

§ 102(e) Date: Aug. 23, 1995

[87] PCT Pub. No.: WO94/18975

PCT Pub. Date: Sep. 1, 1995

[30] Foreign Application Priority Data

Feb. 23, 1993 [JP] Japan .................................. 5-032896

[51] Int. Cl.[6] .................................................. A61K 31/47
[52] U.S. Cl. ............................................ 514/312; 514/912
[58] Field of Search ...................................... 514/312, 912

[56] References Cited

FOREIGN PATENT DOCUMENTS 0382185   8/1990   European Pat. Off. .

*Primary Examiner*—Zohreh Fay
*Attorney, Agent, or Firm*—Sughrue, Mion, Zinn, Macpeak & Seas, PLLC

[57] ABSTRACT

An agent for prophylaxis or treatment of cataract, which comprises as an active ingredient at least one compound selected from a group consisting of a carbostyril compound of the formula:

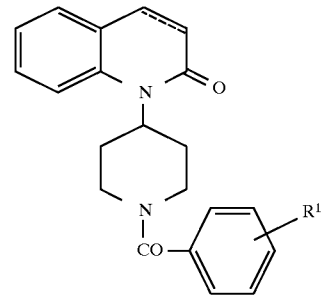

wherein $R^1$ is a lower alkanoylamino-substituted lower alkoxy group, and the bond between the 3- and 4-positions of the carbostyril nucleus is single bond or double bond, or a salt thereof, 5-dimethylamino-1-[4-(2-methylbenzoylamino)benzoyl]-2,3,4,5-tetrahydro-1H-benzazepine and 5-hydroxy-7-chloro-1-[2-methyl-4-(2-methylbenzoylamino)benzoyl]-2,3,4,5-tetrahydro-1H-benzazepine, a method for prophylaxis or treatment of cataract using the same.

5 Claims, No Drawings

AGENT FOR PROPHYLAXIS OR TREATMENT OF CATARACT

This application is a 371 of the PCT/JP94/00265, filed on Feb. 22, 1994.

TECHNICAL FIELD

The present invention relates to an agent for prophylaxis or treatment of cataract comprising as an active ingredient a specific carbostyril compound or benzazepine compound, and a method for prophylaxis or treatment of cataract by using the same.

BACKGROUND ART

The carbostyril and benzazepine compounds used as an active ingredient in this invention have already been known. For example, the carbostyril compounds are disclosed in European Patent Publication No. 0382185 (published on Aug. 15, 1990) and U.S. Pat. No. 5,225,402 (issued on Jul. 6, 1993), wherein it is disclosed that these compounds have vasopressin antagonistic activities and are useful as vasodilator, hypotensive agent, water diuretics, and platelet aggregation inhibitor. The benzazepine compounds are disclosed in WO 91/05549 (published on May 2, 1991) and U.S. Pat. No. 5,258,510 (issued on Nov. 2, 1993), wherein it is disclosed that the compounds have vasopressin antagonistic activities and are useful as vasodilator, hypotensive agent, water diuretics, and platelet aggregation inhibitor. However, it has never been known that the specific carbostyril and benzazepine compounds are effective for the prophylaxis or treatment of cataract.

The present inventors have intensively studied in order to develop a novel agent for prophylaxis or treatment of cataract, and a novel method for prophylaxis or treatment of cataract, and have found that some specific carbostyril compounds and benzazepine compounds are useful in the prophylaxis or treatment of cataract.

Cataract means the condition of the crystalline lens which loses the transparency thereof by storage of water in lens fiber and between lens fibers, or the mass caused by the coagulation of protein, and includes, for example, congenital cataract, or acquired cataracts such as senile cataract, anterior subcapsular cataract, posterior subcapsular cataract, diabetic cataract, cataract accompanying with muscular rigiditic atrophy, irradiation cataract, cataract owing to siderosis, Down's syndrome cataract, Christmas-tree cataract, and the like. Although there are many theories concerning factors causing cataract, for example, disorder in crystalline lens, changes of transparency of lens capsule and lens epithelial, change in ciliary epithelial, i.e. change in chamber water, and the like, it has not been proved yet.

DISCLOSURE OF THE INVENTION

An agent for prophylaxis or treatment of cataract of the present invention comprises as an active ingredient at least one of the compounds selected from a group consisting of a carbostyril compound of the formula:

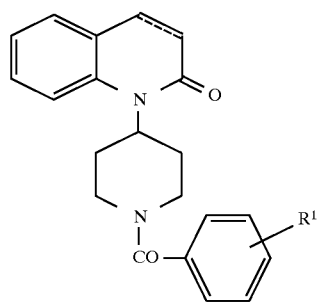

wherein $R^1$ is a lower alkanoylamino-substituted lower alkoxy group, and the bond between the 3- and 4-positions of the carbostyril nucleus is single bond or double bond, a salt thereof, 5-dimethylamino-1-[4-(2-methylbenzoylamino)benzoyl]-2,3,4,5-tetrahydro-1H-benzazepine and 5-hydroxy-7-chloro-1-[2-methyl-4-(2-methylbenzoylamino)benzoyl]-2,3,4,5-tetrahydro-1H-benzazepine.

The "lower alkanoylamino-substituted lower alkoxy group" in the above formula (1) includes a straight chain or branched chain alkoxy group having 1 to 6 carbon atoms which is substituted by a straight chain or branched chain alkanoyl group having 1 to 6 carbon atoms, for example, acetylaminomethoxy, 2-(formylamino)ethoxy, 1-(propionylamino)ethoxy, 3-(butyrylamino)propoxy, 3-(acetylamino)-propoxy, 4-(isobutyrylamino)butoxy, 5-(pentanoylamino)pentyloxy, 6-(hexanoylamino)hexyloxy, and the like.

Among the active compounds (1) of the present invention, the compounds (1) having an acidic group can easily be converted into salts by treating with a pharmaceutically acceptable basic compound. The basic compound includes, for example, alkali metal or alkaline earth metal hydroxides (e.g. sodium hydroxide, potassium hydroxide, lithium hydroxide, calcium hydroxide, etc.), alkali metal carbonates or hydrogen carbonates (e.g. sodium carbonate, sodium hydrogen carbonate, etc.), and alkali metal alcoholates (e.g. sodium methylate, potassium methylate, etc.). Besides, among the active compounds (1) of the present invention, the compounds having a basic group can easily be converted into acid addition salts by treating with a pharmaceutically acceptable acid. The acid includes, for example, inorganic acids (e.g. sulfuric acid, nitric acid, hydrochloric acid, hydrobromic acid, etc.), and organic acids (e.g. acetic acid, p-toluenesulfonic acid, ethanesulfonic acid, oxalic acid, maleic acid, citric acid, succinic acid, benzoic acid, etc.). These salts are also useful in the prophylaxis or treatment of cataract as the active compounds (1).

The active compounds of the present invention show inhibitory activity of development of cataract without decreasing the blood glucose concentration in cataract model produced by streptozotocine (STZ). Thus, the agent of the active compounds of the present invention is useful for the prophylaxis or treatment of various congenital cataract and acquired cataract.

The agent for prophylaxis or treatment of cataract of the present invention are used in the form of a conventional pharmaceutical preparation. The pharmaceutical preparation is prepared by using conventional diluents or carriers such as fillers, thickening agents, binders, wetting agents, disintegrators, surfactants, lubricants, and the like. The pharmaceutical preparation may be selected from various forms in accordance with the desired utilities, and the representative forms are tablets, pills, powders, solutions, suspensions, emulsions, granules, capsules, suppositories, injections (e.g. solutions, suspensions, etc.), ointments, eye drops, and the like.

In order to form in tablets, there are used conventional carriers such as vehicles (e.g. lactose, white sugar, sodium chloride, glucose, urea, starch, calcium carbonate, kaolin, crystalline cellulose, silicic acid, etc.), binders (e.g. water, ethanol, propanol, simple syrup, glucose solution, starch solution, gelatin solution, carboxymethyl cellulose, shellac, methyl cellulose, potassium phosphate, polyvinylpyrrolidone, etc.), disintegrators (e.g. dry starch, sodium alginate, agar powder, laminaran powder, sodium hydrogen carbonate, calcium carbonate, polyoxyethylene sorbitan fatty acid esters, sodium laurylsulfate, stearate monoglyceride, starches, lactose, etc.), disintegration inhibitors (e.g. white sugar, stearin, cacao butter, hydrogenated oil, etc.), absorption promoters (e.g. quaternary ammonium base, sodium laurylsulfate, etc.), wetting agents (e.g. glycerin, starches, etc.), adsorbents (e.g. starches, lactose, kaolin, bentonite, colloidal silicates, etc.), lubricants (e.g. purified talc, stearates, boric acid powder, polyethylene glycol, etc), and the like. The tablets may optionally be in the form of a conventional coated tablet, such as sugar-coated tablets, gelatin-coated tablets, enteric coating tablets, film coating tablets, or double or multiple layer tablets.

In the preparation of pills, the carriers include vehicles (e.g. glucose, lactose, starches, cacao butter, hydrogenated vegetable oil, kaolin, talc, etc.), binders (e.g. gum arabic power, tragacanth powder, gelatin, ethanol, etc.), disintegrators (e.g. laminaran, agar, etc.), and the like.

Capsules may be prepared by charging a mixture of the active compound of the present invention and the above carriers into hard gelatin capsules or soft capsules in usual manner.

In the preparation of injections, the solutions, emulsions and suspensions are sterilized and are preferably made isotonic with the blood. In the preparation of these solutions, emulsions and suspensions, there are used conventional diluents, such as water, ethyl alcohol, macrogol, propylene glycol, ethoxylated isostearyl alcohol, polyoxylated isostearyl alcohol, polyoxylethylene sorbitan fatty acid esters, and the like. In this case, the pharmaceutical preparations may also be incorporated with sodium chloride, glucose or glycerin in an amount sufficient to make them isotonic, and may also be incorporated with conventional solubilizers, buffers, anesthetizing agents.

In the preparation of suppositories, the carriers include, for example, polyethylene glycol, cacao butter, higher alcohols, higher alcohol esters, gelatin, semi-synthetic glycerides, etc.), and the like.

The present eye drops may be prepared by a conventional manner. For example, the present eye drops may be prepared by incorporating the active compound of the present invention into a suitable base, and sterilized. The base includes, for example, sterile purified water.

The present eye drops may contain, if necessary, solubilizer, buffering agent, antioxidant, antiseptic, isotonicity, pH adjuster, and the like. The solubilizer is, for example, sodium carboxymethyl cellulose, polyethylene glycol ethers (e.g. polyoxyethylene lauryl ether, polyoxyethylene oleyl ether), polyethyleneglycol higher fatty acid esters (e.g. polyethylene glycol monolaurate, polyethylene glycol monooleate), polyoxyethylene ether fatty acid esters (e.g. polyoxyethylene sorbitan monolaurate), and the like. The buffering agent is, for example, sodium phosphate, dibasic sodium phosphate, dibasic potassium phosphate, boric acid, sodium borate, citric acid, sodium citrate, tartaric acid, sodium tartrate, acetic acid, sodium acetate, ε-aminocapronic acid, monosodium glutamate, and the like. The antioxidant is, for example, sodium sulfite, sodium pyrosulfite, sodium bisulfite, sodium thiosulfite, ascorbic acid, and the like. The antiseptic is, for example, chlorobutanol, benzalkonium chloride, benzethonium chloride, phenyl mercury salt, thimerosal, phenethyl alcohol, methyl parabene, propyl parabene, and the like. The isotonicity is, for example, sodium chloride, glucose, D-mannitol, glycerin, and the like. The pH adjuster is, for example, sodium hydroxide, hydrochloric acid, and the like.

The present eye drops may be used in the same manner as conventional eye drops, for example, dropping into the eyes from a suitable eye dropper, or spraying onto the eyes with an atomizer.

Besides, the pharmaceutical preparations may optionally be incorporated with a coloring agent, preservatives, perfumes, flavors, sweetening agents, and other medicaments, if required. In the preparation of pastes, creams and gels, there are used conventional diluents, for example, white vaseline, paraffin, glycerin, cellulose derivatives, polyethylene glycol, silicone, bentonite, and the like.

The amount of the active compound of the present invention to be incorporated into the present agent for prophylaxis or treatment of cataract is not specified but may be selected from a broad range, but it is usually in the range of about 1 to 70% by weight, more preferably about 5 to 50% by weight, based on the total weight of the preparation.

The present agent for prophylaxis or treatment of cataract may be administered in any method, and suitable method for administration may be determined in accordance with various forms of preparations, ages, sexes and other conditions of the patients, the degree of severity of diseases to be cured, and the like. For example, tablets, pills, solutions, suspensions, emulsions, granules and capsules are administered orally. The injection are intravenously administered alone or together with a conventional auxiliary liquid (e.g. glucose, amino acid solutions), and further are optionally administered alone in intramuscular, intracutaneous, subcutaneous, or intraperitoneal route, if necessary. Suppositories are administered in intrarectal route. The ointment is applied on the skin.

The dosage of the present agent for prophylaxis or treatment of cataract may be selected in accordance with the administration routes, ages, sexes and other conditions of the patients, the degree of severity of diseases to be cured, and the like, but it may usually be in the range of about 0.6 to 50 mg of the active compound of the present invention per 1 kg of body weight of the patient per day. The active compound is preferably contained in an mount from about 10 to 1000 mg per the dosage unit.

BEST MODE FOR CARRYING OUT THE INVENTION

EXAMPLES

The present invention is illustrated in more detail by the following Preparations of agent for prophylaxis or treatment of cataract, and Experiment of the activities of the active compound of the present invention.

PREPARATION 1

Film coated tablets are prepared from the following components.

| Components | Amount |
| --- | --- |
| 1-{1-[4-(3-Acetylaminopropoxy)-benzoyl]-4-piperidinyl}-3,4-dihydrocarbostyril | 150 g |
| Avicel (trade name of microcrystalline cellulose, manufactured by Asahi Chemical Industries, Co., Ltd.) | 40 g |
| Corn starch | 30 g |
| Magnesium stearate | 2 g |
| Hydroxypropyl methylcellulose | 10 g |
| Polyethylene glycol-6000 | 3 g |
| Castor oil | 40 g |
| Ethanol | 40 g |

The active compound of the present invention, Avicel, corn starch and magnesium stearate are mixed and kneaded, and the mixture is tabletted by using a conventional pounder (R 10 mm) for sugar coating. The tablets thus obtained are coated with a film coating agent consisting of hydroxypropyl methylcellulose, polyethylene glycol-6000, castor oil and ethanol to give film coated tablets.

PREPARATION 2

Tablets are prepared from the following components.

| Components | Amount |
| --- | --- |
| 1-{1-[4-(3-acetylaminopropoxy)benzoyl]-4-piperidinyl}-3,4-dihydrocarbostyril | 150 g |
| Citric acid | 1.0 g |
| Lactose | 33.5 g |
| Dicalcium phosphate | 70.0 g |
| Pluronic F-68 | 30.0 g |
| Sodium laurylsulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium stearate | 3.0 g |
| Dry magnesium stearate | 3.0 g |
| Ethanol | q.s. |

The active compound of the present invention, citric acid, lactose, dicalcium phosphate, Pluronic F-68 and sodium laurylsulfate are mixed. The mixture is screened with No. 60 screen and is granulated with an alcohol solution containing polyvinylpyrrolidone, Carbowax 1500 and 6000. If required, an alcohol is added thereto so that the powder mixture is made a paste-like mass. Corn starch is added to the mixture and the mixture is continuously mixed to form uniform particles. The resulting particles are passed through No. 10 screen and entered into a tray and then dried in an oven at 100° C. for 12 to 14 hours. The dried particles are screened with No. 16 screen and thereto are added dry sodium laurylsulfate and dry magnesium stearate, and the mixture is tabletted to form the desired shape.

The core tablets thus obtained are vanished and dusted with talc in order to guard from wetting. Undercoating is applied to the core tablets. In order to administer the tablets orally, the core tablets are vanished several times. In order to give round shape and smooth surface to the tablets, further undercoating and coating with lubricant are applied thereto. The tablets are further coated with a coloring agent material until the desired colored tablets are obtained. After drying, the coated tablets are polished to obtain the desired tablets having uniform gloss.

PHARMACOLOGICAL TEST

Test compound:
1. 1-{1-[4-(3-Acetylaminopropoxy)benzoyl]-4-piperidinyl}-3,4-dihydrocarbostyril Method The left kidney of Wister male rat (weight; 280–330 g, 9 wk-old) was taken out under ether anesthetization. One week thereafter, a solution of streptozotocine (STZ) in 50 mM citric buffer (pH 4.5) was administered intravenously to the rats on the tail in an amount of 1 ml/kg (i.e. 60 mg of STZ/kg). After the administration of STZ, the rats are separated into two groups, and in one group, a test compound was orally administered to the rats by feeding the rats with feed containing a test compound (0.2%). In another group, the rats were fed with the regular feed (MF) (control group B). Four weeks and 16 weeks after the administration of STZ, the blood glucose concentration in each rat was determined. The results are shown in Table 1.

A controlled-release preparation of insulin (Ultrarente) was administered every two days in an amount of 4 U/body, s.c. Sixteen weeks after the STZ administration, the crystalline lens of the rats were observed with the naked eyes, and if the crystalline lens was observed to be apparently cloud, it was determined to be cataract. The results are shown in Table 2.

Groups

Control A: Normal Wister rats having both kidneys administered with neither STZ nor test compound Control B: Wister rats having no left kidney administered with neither STZ nor test compound Control C: Wister rats having no left kidney administered with STZ but not with test compound Test Compound 1: Wister rats having no left kidney administered with both STZ and Test

TABLE 1

| | Blood Glucose Concentration | |
| --- | --- | --- |
| Groups | After 4 weeks (mg/dl) | After 16 weeks (mg/dl) |
| Control A | 131.4 ± 6.3 | 133.4 ± 8.5 |
| Control B | 126.0 ± 4.0 | 125.4 ± 10.1 |
| Control C | 775.8 ± 41.1 | 670.4 ± 28.1 |
| Test Compound 1 | 801.6 ± 37.9 | 728.9 ± 40.0 |

TABLE 2

| Groups | Number of rats having cataract/ number of all rats in group |
| --- | --- |
| Control A | 0/6 |
| Control B | 0/7 |
| Control C | 7/11* |
| Test Compound 1 | 1/10** |

*: $p < 0.05$, Fisher Exact test
**: $p < 0.05$, Fisher Exact test (based on the data of Control C and Test Compound 1)

As seen from the above data, when STZ alone was administered, the blood glucose level was increased and the cataract was observed in many test animals. On the other hand, the active compound of the present invention was also administered in addition to STZ, the blood glucose level was not decreased but rather increased, however, the cataract was significantly inhibited.

We claim:

1. A method for treatment of cataract comprising administering to a warm-blooded animal in need of cataract treatment a therapeutically effective amount of a composition for treatment of the cataract which comprises as an active ingredient at least one compound selected from the group consisting of a carbostyril compound of the formula:

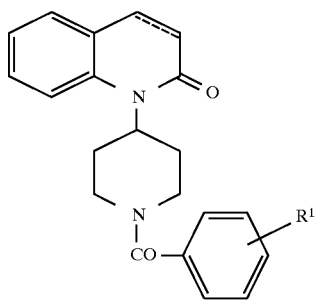

wherein R¹ is a lower alkanoylamino-substituted lower alkoxy group, and the bond between the 3- and 4- positions of the carbostyril nucleus is a single bond or a double bond, or a salt thereof, 5-dimethylamino-1-(4-(2-methylbenzoylamino)benzoyl)-2,3,4,5-tetrahydro-1H-benzazepine and 5-hydroxy-7-chloro-1-(2-methyl-4-(2-methylbenzoylamino)benzoyl)-2,3,4,5-tetrahydro-1H-benzazepine, or a pharmaceutically acceptable salt thereof and a pharmaceutically acceptable carrier or diluent.

2. The method according to claim 1, wherein the active ingredient is the carbostyril compound of the formula:

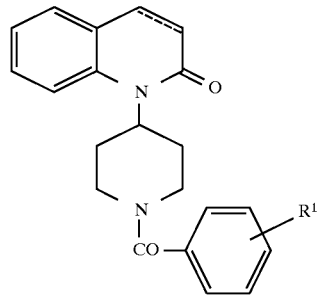

wherein R¹ is a lower alkanoyl-amino-substituted lower alkoxy group, and the bond between the 3- and 4-positions of the carbostyril nucleus is a single bond or a double bond, or a salt thereof.

3. The method according to claim 1, wherein the active ingredient is 5-dimethyl-1-(4-(2-methylbenzoylamino) benzoyl)-2,3,4,5-tetrahydro-1H-benzazepine or 5-hydroxy-7-chloro-1-(2-methyl-4-(2-methylbenzoylamino)benzoyl)-2, 3,4,5-tetrahydro-1H-benzazepine or a pharmaceutically acceptable salt thereof.

4. The method according to claim 2, wherein the active ingredient is 1-{1-(4-(3-acetylaminopropoxy)benzoyl)-4-piperidinyl}-3,4-dihydrocarbostyril or a salt thereof.

5. The method according to claim 2, wherein R¹ in the carbostyril compound is selected from the group consisting of acetylaminomethoxy, 2-(formylamino)ethoxy, 1-(propionylamino)-ethoxy, 3-(butylamino)propoxy, 3-(acetylamino)propoxy, 4-(isobutyrylamino)butoxy, 5-(pentanoylamino)pentyloxy and 6-(hexanoylamino) hexyloxy, or a salt thereof.

* * * * *